United States Patent [19]
Rocklage et al.

[11] Patent Number: 5,833,947
[45] Date of Patent: Nov. 10, 1998

[54] MAGNETIC RESONANCE IMAGING

[75] Inventors: Scott M. Rocklage, Los Gatos; John Kucharczyk, Mill Valley; Michael E. Moseley, San Francisco, all of Calif.

[73] Assignee: The Regents of the University of California, Oakland, Calif.

[21] Appl. No.: 604,778

[22] Filed: Feb. 23, 1996

Related U.S. Application Data

[62] Division of Ser. No. 306,221, Sep. 14, 1994, Pat. No. 5,494,655, which is a continuation of Ser. No. 946,373, which is a continuation of PCT/EP91/00443 Mar. 6, 1991 WO91/14186 Sep. 19, 1996, abandoned, which is a continuation of Ser. No. 490,859, Mar. 9, 1990, Pat. No. 5,190,744.

[51] Int. Cl.$^6$ .................................................. A61B 5/055
[52] U.S. Cl. ................. 424/9.36; 424/9.363; 424/9.364; 514/836; 128/653.3
[58] Field of Search ............................... 424/9.36, 9.363, 424/9.364, 9.365; 324/306.309; 436/173; 128/653.4, 654, 653.3; 514/184, 492, 502, 836

[56] References Cited

U.S. PATENT DOCUMENTS

| 4,639,365 | 1/1987 | Sherry et al. | 424/9 |
| 4,647,447 | 3/1987 | Gries et al. | 424/9 |
| 4,687,658 | 8/1987 | Quay et al. | 424/9 |
| 4,687,659 | 8/1987 | Quay et al. | 424/9 |

FOREIGN PATENT DOCUMENTS

| 87/76217 | 2/1988 | Australia . |
| 88/10649 | 7/1988 | Australia . |
| 88/14611 | 10/1988 | Australia . |
| 1253514 | 5/1989 | Canada . |
| 0186947 | 9/1986 | European Pat. Off. . |
| 0232751 | 8/1987 | European Pat. Off. . |
| 0292689 | 11/1988 | European Pat. Off. . |
| 0299795 | 1/1989 | European Pat. Off. . |
| 0230893 | 6/1990 | European Pat. Off. . |
| 85/04330 | 10/1985 | WIPO . |
| 85/05554 | 12/1985 | WIPO . |
| 88/00060 | 1/1988 | WIPO . |
| 89/06979 | 8/1989 | WIPO . |
| 89/09625 | 10/1989 | WIPO . |

*Primary Examiner*—Gary E. Hollinden
*Attorney, Agent, or Firm*—Lyon & Lyon LLP

[57] ABSTRACT

The invention provides a method of monitoring the vasodilatory or vasoconstrictive effects of a physiologically active substance administered to a human or non-human animal body, said method comprising the steps of: administering said substance into said body; administering into the systemic vasculature of said body a contrast enhancing amount of an intravascular paramagnetic metal containing magnetic resonance imaging contrast agent; subjecting said body to a magnetic resonance imaging procedure capable of generating from magnetic resonance signals from said body a series of temporally spaced images of at least a part of said body into which said agent passes, said procedure being a fast imaging procedure having an image acquisition time of less than five seconds; and detecting temporal variations in said signals or images whereby to monitor the vasoconstriction or vasodilation induced by said substance.

21 Claims, 7 Drawing Sheets

MAGNETIC RESONANCE IMAGING

This application is a divisional of Ser. No. 08/306,221, filed Sep.14, 1994, now U.S. Pat. No. 5,494,655, which is a continuation of Ser. No. 07/946,373, filed Oct. 30, 1992, now abandoned, which is a 371 of PCT/EP91/00443 filed Mar. 6, 1991, which is a continuation of U.S. application Ser. No. 07/490,859, filed Mar. 9, 1990, now U.S. Pat. No. 5,190,744.

FIELD OF THE INVENTION

This invention relates to improvements in and relating to magnetic resonance imaging, in particular imaging of phenomena associated with blood flow variations and abnormalities.

BACKGROUND OF THE INVENTION

Magnetic resonance imaging (MRI) has been used successfully to study blood flow in vivo. Moreover Villringer et al. Magnetic Resonance in Medicine 6:164–174 (1988), Cacheris et al. Society of Magnetic Resonance in Medicine, 7th Annual Meeting, San Francisco, 1988, (SMRM 1988) Works in Progress, page 149 and Belliveau et al. SMRM 1988, Book of Abstracts, page 222 have proposed the use of certain paramagnetic lanthanide chelates as magnetic susceptibility, that is $T_2^*$ shortening, MRI contrast agents for studies of cerebral blood flow and perfusion.

Unlike many previous imaging procedures, $T_2$ or $T_2^*$-weighted MRI using magnetic susceptibility (MS) contrast agents (hereinafter MS imaging) enabled blood perfusion deficits, e.g. cerebral ischemias, to be visualized rapidly as the MR signal intensity was reduced in the regions of normal perfusion due to the effect of the contrast agent, with ischemic tissue being revealed by its retention of signal intensity.

Blood perfusion deficits are associated with several serious and often life-threatening conditions. Rapid identification and location of such deficits is highly desirable in order that the appropriate corrective action, be it therapeutic or surgical, may be taken promptly. Thus in the case of cerebral ischemia, any delay in post ischemic recirculation and reoxygenation of brain tissue reduces neuronal survivability.

MS imaging therefore represents a major improvement over routine $T_2$ or $T_2^*$-weighted imaging in the absence of MS contrast agents, since in the routine procedures ischemias or infarcts only become detectable 2 to 3 hours after the event, e.g. a stroke, which gave rise to the perfusion deficit. However, while determination of the existence and location of a perfusion deficit is important, it is also desirable to be able to detect the degree or severity, and if possible the onset and duration of blood flow abnormalities or variations, in a quantifiable manner. We now propose that this be done using a modified MS imaging procedure.

SUMMARY OF THE INVENTION

Viewed from one aspect the invention provides a method of detecting blood flow abnormality or variation in a human or non-human, especially mammalian, body, said method comprising administering into the systemic vasculature of a said body a contrast enhancing amount of an intravascular paramagnetic metal, e.g. transition metal or lanthanide, containing magnetic resonance imaging contrast agent, subjecting said body to a magnetic resonance imaging procedure capable of generating from magnetic resonance signals from said body a series of temporally spaced images of at least a part of said body into which said agent passes, and detecting temporal variations in said signals or images whereby to identify regions of abnormal or modified blood flow in said body and to indicate the degree of blood flow abnormality or modification therein.

Thus the method of the invention provides a quantitative and temporal determination of local perfusion variations, e.g. deficits or increases, which may arise from, for example, stroke, microsurgery or administration of blood flow modifying pharmaceuticals.

The method of the present invention is preferably carried out using spin-echo techniques. Alternatively and also preferably the method may be carried out using a so-called fast or ultra fast imaging technique in order to enable a series of $T_2^*$ dependent images to be generated with as short as possible a time interval between successive images. For this reason, techniques capable of generating images with time intervals of less than 5 seconds, especially less than 0.5 seconds and more especially less than 100 milliseconds, are particularly preferred. Thus, in general, techniques such as spin echo, gradient echo, TurboFLASH, and most especially the various varieties of echo planar imaging (EPI), are particularly suitable for use in accordance with the method of the invention.

In the method of the invention, an indication of the degree of blood flow abnormality or modification for a given voxel may readily be determined by comparison of the MR signal intensity for that voxel with a reference value, e.g. the signal intensity for similar tissue with normal blood flow. The reference intensity values may be predetermined or may be selected as the MR signal intensity values for voxels of normal tissue in the same image. In the case of cerebral ischaemias, signal intensity values from the normally perfused gray matter and white matter of the brain may be used to provide reference values for the affected tissue. As is discussed in further detail below, the location and spatial extent of the blood flow abnormalities, and the location and spatial extent of the regions having the most severe blood flow abnormalities detected in this way according to the method of the invention, correspond closely to the same extents and locations as determined using conventional non-MRI techniques such as histopathologic tissue-staining and quantitative autoradiography.

In one particularly preferred embodiment of the invention, temporally spaced images are generated following repeated administrations of the MS contrast agent, e.g. at intervals of no less than 15–30 minutes, whereby to detect the time of onset and thereafter to monitor the development of the blood flow abnormality or modification, e.g. to identify the extent and location of reperfusable tissue and the degree of success of reperfusion, or to identify tissue for which surgical intervention is required before reperfusion is possible.

Thus the method of the invention may be used to characterize quantitatively the regional microcirculation of the brain before and after acute arterial occlusion and differentiate between regions with normal blood flow, reduced blood flow and no blood flow. With the different distributions of MS contrast media in occluded and reperfused cerebral tissues, the method may also be used to document reperfusion of ischemic tissue. Moreover, with the use of MS contrast media in the method of the invention, distinction can be made between central cores of necrosis and the surrounding penumbrae of salvageable tissue, i.e. between irreversibly and reversibly injured brain tissue. Using ultrafast imaging techniques in the method of the present invention, the kinetics of the distribution of the contrast medium into tissue and of the wash-out of the contrast medium from the tissue can be followed so as to provide a diagnostic "signature" which could be used to distinguish between normal, ischemic, infarcted and reperfused tissue and to characterize the type of ischemic event and to identify tissues at risk from ischemia.

In one embodiment of the method of the invention, using a fast imaging procedure, the determination of the location and severity of ischaemia is effected by determining the time dependence of the MR signal intensity for the voxels in the seconds following administration of the contrast agent, and generating an image where voxel image intensity value is dependent on the time post-administration at which MR signal intensity for that voxel is lowest. Normal tissue reaches minimum MR signal intensity sooner than ischaemic tissue, and the resulting image thus enables the spatial extent and local severity of blood flow abnormality to be visualized. Alternatively, a similar image may be generated by making the voxel image intensity value dependent on the time taken before voxel MR signal intensity reattains a pre-selected control value, e.g. its pre-injection value or a percentage of that value (for example 80%).

The contrast agent used according to the method of the invention should be an intravascular contrast agent, that is to say one which is substantially retained within the systemic vasculature at least until it has passed through the body region or organ of particular interest. Generally, therefore, blood pooling, particulate and hydrophilic contrast agents or contrast agents possessing more than one of these properties are of particular interest.

Besides its obvious application in terms of identifying and giving an indication of the severity of cerebral or cardiac ischemias or infarcts, the method of the present invention has a broad range of possible diagnostic and evaluative applications of which the following list names but a few:

Assessment of cerebral perfusion in brain dysfunction associated with acute severe symptomatic hyponatremia;

Evaluation of new therapies (for example thrombolytic therapies and clot removal, calcium channel blockers, anti-inflammatory agents, angioplasty, etc) in the treatment of cerebral vasospasm;

Assessment of cerebral perfusion following induced subarachnoid haemorrhage;

Assessment of different degrees of ischemia in large tissue masses;

Study of the relationship between blood ammonia, lactate, pH and cerebral perfusion in cerebral ischemia associated with acute liver failure (this has implications for the treatment of Alzheimer's disease);

Localisation and assessment of thrombus and plaque;

Evaluation of new therapies for stroke (for example t-PA, aspirin antiphospholipids/lupus anticoagulants, antiphospholipid antibodies, etc);

Evaluation of risk factors for stroke (for example elevated serum lipids, etc);

Assessment of the impact of induced brain hypothermia on cerebral perfusion during neurosurgery for stroke;

Assessment of the effects of ageing on cerebral perfusion including the study of the etiology of lacunar infarcts;

Assessment of the effects of cocaine, amphetamine and ethanol on cerebral perfusion in mildly and severely ischemic brain;

Definition of the "therapeutic window" in reversible focal ischemia for heparin, vasodilators, antihypertensives and calcium antagonists; and Monitoring of other induced vasodilator effects.

Thus viewed from a further aspect the invention provides a method of detecting and quantitatively evaluating the severity of ischemias in a human or non-human, especially mammalian, body, said method comprising administering into the systemic vasculature of said body a contrast enhancing amount of an intravascular paramagnetic metal containing magnetic susceptibility magnetic resonance imaging contrast agent, subjecting said body to a magnetic resonance imaging procedure capable of generating from magnetic resonance signals from said body a series of temporally spaced images of at least a part of said body into which said agent passes, and detecting temporal variations in said signals or images whereby to detect ischemic tissue and to provide a quantitative indication of the degree of blood perfusion deficit therein.

Viewed from a still further aspect, the present invention also provides a method of monitoring the vasodilatory or vasocontractory effects of a physiologically active substance administered to a human or non-human animal body, for example a calcium antagonist, said method comprising administering said substance into said body, administering into the system vasculature of said body a contrast enhancing amount of an intravascular paramagnetic metal containing magnetic susceptibility magnetic resonance imaging contrast agent, subjecting said body to a magnetic resonance imaging procedure capable of generating from magnetic resonance signals from said body a series of temporally spaced images of at least a part of said body into which said agent passes, and detecting temporal variations in said signals or images whereby to monitor the vasoconstriction or vasodilation induced by said substance.

Viewed from a still further aspect, the present invention also provides a method of monitoring surgically induced blood perfusion variations, either before or during surgery, said method comprising administering a contrast enhancing amount of an intravascular paramagnetic metal containing magnetic susceptibility magnetic resonance imaging contrast agent into the systemic vasculature of a human or animal body which is undergoing or has undergone surgery, in particular microsurgery on said vasculature, subjecting said body to a magnetic resonance imaging procedure capable of generating from magnetic resonance signals from said body a series of temporally spaced images of at least a part of said body into which said agent passes, and detecting temporal variations in said signals or images whereby to identify regions of surgically induced variations in blood perfusion.

Viewed from a still further aspect the invention provides the use of a MS contrast agent for the manufacture of a contrast medium for use in the methods of the invention.

DETAILED DESCRIPTION OF THE INVENTION

Figure 1:
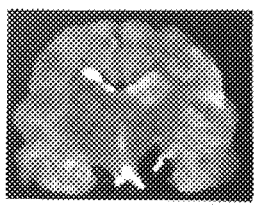
FIGS. 1–9 show $T_2$-weighted spin-echo images of a cat brain (FIGS. 1–3), hyperintensity contour plots derived therefrom (FIGS. 4–6), and superimposed versions (FIGS. 7–9), acquired at 108, 160 and 320 minutes following unilateral MCA occlusion and subsequent reperfusion (see Study 2).

The magnetic susceptibility, $T_{2^*}$-reducing effect, of MS contrast agents is to a large degree dependant on the magnitude of the magnetic moment of the magnetic species within the contrast agent—the higher the magnetic moment the stronger the effect. Indeed the effect is approximately proportional to the square of the magnetic moment making the effect of Dy(III) about 1.95 times larger than that of Gd(III). In general paramagnetic metal species having magnetic moments of $\geq 4$ BM will be preferred. The contrast agents particularly preferred for use in the method of the present invention are those containing paramagnetic lanthanide ions, especially high spin lanthanides such as ions of Dy, Gd, Eu, Yb and Ho, in particular Dy(III).

In order that they may be administered at effective but non-toxic doses, such paramagnetic metals will generally be administered in the form of ionic or much more preferably non-ionic, complexes, especially chelate complexes optionally bound to larger carrier molecules which may be selected to manifest greater residence times in plasma, or to enhance the blood pooling nature of the contrast agent or to reduce the osmolality of the contrast medium by increasing the number of paramagnetic centres per contrast agent molecule (or molecular ion).

A wide range of suitable chelants, polychelants, and macromolecule bound chelants for paramagnetic metal ions has been proposed in the patent literature over the last decade and in this respect particular regard may be had to US-A-4647447 (Gries), US-A-4687659 (Quay), US-A-4639365 (Sherry), EP-A-186947 (Nycomed), EP-A-299795 (Nycomed), WO-A-89/06979 (Nycomed), EP-A-331616 (Schering), EP-A-292689 (Squibb), EP-A-232751 (Squibb), EP-A-230893 (Bracco), EP-A-255471 (Schering), EP-A-277088 (Schering), EP-A-287465 (Guerbet), WO-A-85/05554 (Amersham) and the documents referred to therein, the disclosures of all of which are incorporated herein by reference.

Particularly suitable chelants for the formation of paramagnetic metal chelate MS contrast agents for use in the method of the present invention include the following:

N,N,N',N'',N''-diethylenetriaminepentaacetic acid (DTPA), 6-carboxymethyl-3,9-bis(methylcarbamoylmethyl)-3,6,9-triazaundecanedioic acid (DTPA-BMA), 6-carboxymethyl-3,9-bis(morpholinocarbonylmethyl)-3,6,9-triazaundecanedioic acid (DTPA-BMO), 1,4,7,10-tetraazacyclododecane-N,N',N'',N'''-tetraacetic acid (DOTA), 1,4,7,10-tetraazacyclododecane-N,N',N''-triacetic acid (DO3A), 1-(2-hydroxypropyl)-1,4,7,10-tetraazacyclododecane-N,N',N'',N'''-triacetic acid (HP-DO3A), 1-oxa-4,7,10-triazacyclododecane-N,N',N''-triacetic acid (OTTA), polylysine-bound DTPA and DTPA derivatives or DO3A and DO3A derivatives or DOTA and DOTA derivatives (eg. DTPA-polylysine, DO3A-polylysine and DOTA-polysine), soluble dextran-bound DTPA and DTPA derivatives having with a total molecular weight $\geq 40$ KD, preferably in the range 60–100 KD (DTPA-dextran).

Particularly suitable paramagnetic metal ions for chelation by such chelates are ions of metals of atomic numbers 21 to 29,42,44 and 57 to 71, especially 57 to 71, more especially Cr, V, Mn, Fe, Co, Pr, Nd, Eu, Gd, Tb, Dy, Ho, Er, Tm, Yb and Ln, in particular Cr(III), Cr(II), V(II), Mn(III), Mn(II), Fe(III), Fe(II) and Co(II) and especially Gd(III), Tb(III), Dy(III), Ho(III), Er(III), Tm(III) and Yb(III) especially Dy(III), Ho(III) and Er(III).

All paramagnetic ions have both $T_1$ and $T_2$ reducing effects on the surrounding non-zero spin nuclei and as the effect on MR signal intensity of these two effects is generally opposed in unweighted images, $T_1$ reduction leads to image intensity increases whereas $T_2$ reduction leads to image intensity losses. Thus for the purposes of the present invention it is particularly preferred to use paramagnetic metals which have relatively poor $T_1$-relaxivity in order to maximize the MR effect of the contrast agents in $T_2^*$ or $T_2$ weighted MR imaging. Thus Dy(III) or even Yb(III) would generally be used in preference to Gd(III).

In order to perform the method of the invention with as high as possible a safety factor, the ratio between the dose of the contrast agent and its $LD_{50}$, it is particularly preferred to use non-ionic or low osmolality chelates, i.e. chelates which carry no overall ionic charge, such as Dy DTPA-BMA for example, or where the complex has an overall ionic charge to paramagnetic metal centre ratio of 1.5 or less.

Furthermore, to ensure that the contrast agent remains wholly or essentially within the blood vessels during passage through the body region of interest, the contrast agent will as mentioned above preferably be hydrophilic and retained in the vasculature for a sufficiently long time to permit effective imaging.

Examples of suitable blood-pooling agents include the inert soluble macromolecule-bound chelates of the type described by Nycomed in EP-A-186947 and WO-A-89/06979. Binding the chelant to a macromolecule, e.g. a polysaccharide such as dextran or derivatives thereof, to produce a soluble macromolecular chelant having a molecular weight above the kidney threshold, about 40 KD, ensures relatively long term retention of the contrast agent within the systemic vasculature.

Examples of suitable hydrophilic contrast agents include linear, branched or macrocyclic polyamino-carboxylic acid chelates of paramagnetic metal ions, especially chelates of chelants in which carboxylic acid groupings are replaced by hydrophilic derivatives thereof, such as amides, esters or hydroxamates, or in which the chelant backbone is substituted by hydrophilic groupings such as for example hydroxyalkyl or alkoxyalkyl groups. Chelants of this type are disclosed for example in US-A-4687658 (Quay), US-A-4687659 (Quay), EP-A-299795 (Nycomed) and EP-A-130934 (Schering).

Particular mention however must be made of the Dy(III), Ho(III) and Er(III) chelates of DTPA-BMA, DTPA-BMO, and DO3A and HP-DO3A.

The dosages of the contrast agent used according to the method of the present invention will vary according to the precise nature of the contrast agent used. Preferably however the dosage should be kept as low as is consistent with still achieving an image intensity reduction in $T_2^*$-weighted imaging. Thus for Dy(III) based chelates, for example, dosages of Dy of 0.05 to 0.5 mmol/kg bodyweight, and especially 0.08 to 0.3 mmol/kg, are particularly preferred. In this way not only are toxicity-related problems minimized but the sensitivity of the imaging method towards the detection of ischemia of varying degrees of severity is increased. At higher dosages the signal suppression by the MS contrast agent may be unduly abrupt and intense, making regions with relatively minor perfusion deficits appear to have the characteristics of relatively normal blood flow. For most MS contrast agents the appropriate dosage will generally lie in the range 0.02 to 3 mmol paramagnetic metal/kg bodyweight, especially 0.05 to 1.5 mmol/kg, particularly 0.08 to 0.5, more especially 0.1 to 0.4 mmol/kg. It is well within the skill of the average practitioner in this field to determine the optimum dosage for any particular MS contrast agent by relatively routine experiment, either in vivo or in vitro.

Where the contrast agent is ionic, such as is the case with Dy DTPA, it will conveniently be used in the form of a salt with a physiologically acceptable counterion, for example an ammonium, substituted ammonium, alkali metal or alkaline earth metal cation or an anion deriving from an inorganic or organic acid. In this regard, meglumine salts are particularly preferred.

Contrast agents may be formulated with conventional pharmaceutical or veterinary aids, for example stabilizers, antioxidants, osmolality adjusting agents, buffers, pH adjusting agents, etc., and may be in a form suitable for injection or infusion directly or after dispersion in or dilution with a physiologically acceptable carrier medium, e.g. water for injections. Thus the contrast agents may be formulated in conventional administration forms such as powders, solutions, suspensions, dispersions etc., however solutions, suspensions and dispersions in physiologically acceptable carrier media will generally be preferred.

The contrast agents may therefore be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized. Suitable additives include, for example, physiologically biocompatible buffers (as for example DTPA or DTPA-bisamide (e.g. 6-carboxymethyl-3,9-bis(methylcarbamoylmethyl)-3,6,9-triazaundecanedioic acid)) or calcium chelate complexes (as for example calcium DTPA salts, calcium DTPA-bisamide salts or NaCaDTPA-bisamide) or, optionally, additions (e.g. 1 to 50 mole percent) of calcium or sodium salts (for example, calcium chloride, calcium ascorbate, calcium gluconate or calcium lactate and the like).

Parenterally administrable forms, e.g. intravenous solutions, should of course be sterile and free from physiologically unacceptable agents, and should have low osmolality to minimize irritation or other adverse effects upon administration and thus the contrast medium should preferably be isotonic or slightly hypertonic. Suitable vehicles include aqueous vehicles customarily used for administering parenteral solutions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the contrast agents and which will not interfere with the manufacture, storage or use of products.

In the method of the present invention where the lanthanide has any significant $T_1$-reducing effect, which is especially the case where the paramagnetic metal is Gd rather than Dy, this $T_1$-reducing effect may also be utilised to increase the degree of certainty with which perfused regions are identified by generating corresponding $T_1$ weighted images and determining the signal ratio for each pixel or voxel between the two types of image. In this way tissue with very limited perfusion may perhaps be distinguished from tissue in which blood flow has ceased entirely. Where such a technique is used however it will be especially desirable to use the low toxicity, low osmolar forms of the paramagnetic complex in order to operate with as large a safety factor as possible. Thus for Gd it will generally be preferably to use GdHP-DO3A, GdDO3A, GdDTPA-BMA or GdDTPA-BMO rather than GdDOTA or GdDTPA salts.

Generally data manipulation forms a major part of the method of the invention since information regarding the severity of perfusion deficit may be extracted from the rate at which signal intensity loss takes place for the region of interest following MS contrast agent administration (the less obstructed the blood flow the more rapidly the signal is lost) and the duration and magnitude of signal loss. Clearly comparison with data obtained for healthy tissue will enable a form of perfusion calibration to be made. Moreover indications of the blood volume affected may also be obtained by measurement of the area under the curve for a plot of pixel or voxel signal intensity loss over time for the duration of the MS contrast agent induced signal loss. The necessary data manipulation, including display of zones of reduced or enhanced perfusion optionally superimposed on a selected background image, e.g. the "native" image obtained in the absence of the MS contrast agent, can of course be performed by a computer, generally the same computer as is arranged to operate the MR imager and generate MR images from the detected MR signals.

The methods of the invention are particularly suited to the early detection of ischaemias as ischaemic events may in this way be detected significantly less than 1 hour after occurrence, as opposed to the 2–3 hours or more of conventional $T_2$ weighted MRI, so making it possible to take steps to reperfuse the affected tissue at an earlier stage or to treat it with a cerebroprotective pharmaceutical, and thus raising the chances of reducing permanent tissue damage and of increasing tissue survivability.

The method of the invention will now be described further by way of example with particular reference to certain non-limiting embodiments and to the accompanying drawings in which FIGS. 1 to 24 are images or diagrams of the cat brain before, during or after unilateral MCA occlusion.

Study 1

Young adult cats weighing 2.0 to 4.5 kg were anaesthetized with 30 mg/kg i.v. Nembutal. Polyethylene catheters were placed in the femoral artery and vein for blood pressure monitoring and drug administration. The right middle cerebral artery (MCA) was isolated via the transorbital approach and occluded just proximal to the origin of the lateral striate arteries with bipolar electrocautery followed by complete surgical transection. The dural incision and orbit were covered with saline moistened gauze and absorbable gelatin sponge.

A General Electric CSI (2 Tesla) unit, equipped with Acustar S-150 self-shielded gradient coils (±20 gauss/cm, 15 cm bore size) was used. MRI was performed with an 8.5 cm inner-diameter low-pass birdcage proton imaging coil. Successive multislice $T_2$-weighted coronal images were obtained for up to 12 hours following occlusion. Spin-echo $T_2$-weighted images (TR 2800, TE 80 and 160, 3 mm slices, 1 mm gap) were obtained with a field-of-view (FOV) of 80 mm in which two scans were averaged for each one of the 128 phase-encoding steps resulting in a total acquisition time of 12 minutes.

In order to evaluate the anatomic region of perfusion deficiency following MCA occlusion, cats were injected with a non-ionic T2*-shortening contrast agent, DyDTPA-BMA. The DyDTPA-BMA complex was prepared by refluxing an aqueous suspension containing stoichiometric amounts of dysprosium oxide and DTPA-BMA. The contrast agent was infused i.v. at doses of 0.25, 0.5 or 1.0 mmol/kg beginning at phase-encoding step #32 and finishing at step #60 (approximately 3 min) of $T_2$-weighted image acquisition. DyDTPA-BMA injections were given at different time points post MCA occlusion in individual cats. After injection, the magnetic susceptibility effect was quantified for up to 60 minutes in both ischemic and normal hemispheres by comparing region-of-interest (ROI) intensity to pre-contrast $T_2$-weighted ROI intensities. ROI image analyses were carried out in the ischemic inferior parietal gyrus, caudate, putamen, and internal capsule, and compared with the corresponding uninjured contralateral regions. A signal intensity ratio was calculated as the ROI image intensity ratio of an abnormal, ischemic region over that of the normal, contralateral side. Results were expressed as the mean percentage change±Standard Error of the Mean (X±S.E.M.)

At the conclusion of the MR protocol, 15 ml/kg of a 2% solution of 2,3,5-triphenyl tetrazolium chloride (TTC) was infused transcardially. The brain was removed from the cranium after 10–20 minutes, immersed in a 2% TTC solution for another 10–20 minutes, and then stored overnight in 10% buffered formalin in a light shielded container. The brain was sectioned coronally (2–3 mm slices) from 24–36 hours later and immediately examined for histologic evidence of ischemic damage as evidenced by pallor of TTC-staining.

Using a 0.5 mmol/kg dosage of DyDTPA-BMA, maximum signal intensity losses of 35% were observed in the gray matter of the normal non-occluded cerebral hemisphere during the first 15 minutes after injection. Signal intensity changes in white matter (internal capsule) in both the normal and ischemic hemispheres were smaller than in gray matter, presumably because of higher cerebral blood flow to gray matter. The resulting contrast-enhanced images had superior gray/white matter contrast than $T_2$-weighted spin-echo MR images without contrast. At 45 minutes after administration of DyDTPA-BMA, signal intensity had recovered to at least 90% of pre-contrast control values in all cerebral tissues. Increasing the dosage of DyDTPA-BMA from 0.5 to 1.0 mmol/kg produced only a minimal difference in immediate post-contrast signal intensity. Long TE times (160 msec) produced the highest gray/white matter contrast after DyDTPA-BMA at each of the 3 doses tested. (In general in the method of the invention using higher TE values leads to a slight loss in signal to noise ratio but also to increased sensitivity to $T_2$*-induced proton dephasing and hence to the MS contrast agent).

Perfusion deficits resulting from occlusion of the MCA were detected as regions of signal hyperintensity of the occluded ischemic tissue compared to the normally perfused areas in the contralateral hemisphere. Relative hyperintensity was found in the occluded basal ganglia as early as 30 minutes post-occlusion for both the 1 mmol/kg and 0.5 mmol/kg dosages. Signal differences between ischemic and contralateral control tissues were observed for gray matter in the inferior parietal gyrus (42±14%), and basal ganglia (26±8%), and to a lesser extent, for the white matter in the internal capsule (5±4%). By comparison, $T_2$-weighted MRI without contrast failed to demonstrate any significant signal differences prior to approximately 2–3 hours post MCA occlusion (see Table 1). As well, DyDTPA-BMA administration allowed detection of small developing infarcts that were not visible or were ambiguous on $T_2$-weighted images without contrast (see Table 2).

TABLE 1

Effect of DyDTPA-BMA administration on the time of detection of cerebral ischemic damage.

| Dose DyDTPA-BMA | # | Onset of signal hypertensity (relative to pre-contrast $T_2$-weighted image) | | |
|---|---|---|---|---|
| (mmol/kg) | Cats Tested | Earlier | Same Time | Later |
| 0.25 | 5 | 1 | 4 | 0 |
| 0.50 | 16 | 12 | 4 | 0 |
| 1.0 | 6 | 4 | 2 | 0 |

TABLE 2

Effect of DyDTPA-BMA administration on the definition of injury site (signal intensity ratio of injured tissue to corresponding contralateral control tissue) compared to pre-contrast $T_2$-weighted image.

| Dose DyDTPA-BMA | # injections | Signal intensity ratio (relative to pre-contrast $T_2$ weighted image) | | |
|---|---|---|---|---|
| (mmol/kg) | contrast | Better | Same | Worse |
| 0.25 | 5 | 4 | 1 | 0 |
| 0.50 | 23 | 17 | 6 | 0 |
| 1.0 | 16 | 14 | 2 | 0 |

Within 3–5 hours after MCA occlusion, $T_2$-weighted images also demonstrated tissue injury clearly, including increased mass-effect and hyperintensity (edema) throughout the MCA territory. The distribution of increased signal intensity correlated well anatomically with regions of perfusion deficiency demonstrated with DyDTPA-BMA-enhanced MR imaging. A continuing close anatomic correspondence between areas of perfusion deficit and edematous regions was seen 9 hours and 11 hours post occlusion. In subsequent TTC-stained coronal sections, these areas were found to exhibit characteristics typical of ischemic tissue injury, such as pallor of staining, coagulation, necrosis, and glial proliferation.

These results confirm that MS contrast agent enhanced MRI can significantly advance the time of detection of cerebral ischemic insults. Evidence of stroke-induced perfusion deficits was observed in the MCA territory as early as 45 minutes post-occlusion using contrast-enhanced MRI, whereas $T_2$-weighted spin-echo images without contrast did not demonstrate increased signal intensity until 2–3 hours after occlusion.

Contrast in $T_2$-weighted spin-echo MRI can be produced by changes in the microscopic magnetic fields experienced by protons undergoing molecular diffusion. These field gradients cause spin dephasing and loss of spin echo signal intensity. Field gradients arise at the interface of two volumes with different magnetic susceptibilities and thus different induced magnetic fields.

The presence of paramagnetic chelates can alter the magnetic susceptibility of tissue. In the brain, since the chelates are confined to the intravascular space by the blood-brain barrier, a field gradient is induced between the capillary space and surrounding (perfused) tissue resulting in significant signal loss. These results show that this approach to MR contrast enhancement can be used to differentiate ischemic from normally perfused regions.

A further notable advantage of the method of the invention is its relative insensitivity to motion compared to diffusion-weighted MR imaging. Given the relatively high safety index ($LD_{50}$ i.v. administration in mice is 34 mmol/kg), the long duration of the magnetic susceptibility effect of DyDTPA-BMA and its negligible $T_1$-reducing effect makes this a particularly good MS contrast agent for use with $T_2$-weighted MRI.

The contrast-enhanced images suggested considerable regional heterogeneity in perfusion throughout the ischemic MCA territory. Post-contrast signal hyperintensity was observed earlier in the basal ganglia than the neocortex. This finding suggests that non-anastomosing end-arterial tissues, such as the caudate and putamen, are most susceptible to post-ischemia perfusion deficits, since no collateral circulation is available. In collaterally perfused areas such as neocortex, on the other hand, tissue injury may be mitigated somewhat by continued blood flow in the partially ischemic watershed regions. It seems likely that the method of the invention may be able to help identify normal and abnormal regional blood flow differences, and especially to differentiate reversibly ischemic penumbra from infarcted tissue based on the degree and duration of perfusion deficit to cerebral tissues.

In further studies of cerebral perfusion deficits on the cat MCA model described above, using echo planar imaging in conjunction with low, ie. 0.1 and 0.15 mmol/kg, dosages of DyDTPA-BMA, quantitative spatial and temporal assessment of stroke affected tissue may be made. This dosage reduction further increases both the potential sensitivity and the safety profile of the method of the invention.

The advantage of using echo planar MRI with a MS contrast agent is that images may be acquired continuously before, during and after contrast injection. This allows the time course of the contrast agent passage through a tissue to be monitored and to obtain images at the maximum contrast dosage. Since the echo-planar pulse sequence does not require a 180° refocussing pulse, the $T_2^*$ effects of the MS contrast agent are accentuated.

Echo planar images on the GE CSI 2 Tesla were acquired in a sequential fashion. Sixteen images were obtained one each second or less, each image possessing a 66 msec acquisition time with a data matrix of 64×64 pixels over a 60×60 mm field-of-view. The slice thickness was 3 mm. The echo-planar sequence was that of a gradient-echo nature, with the time of echo (TE) value adjusted to maximise the $T_2^*$-shortening contrast effect.

Study 2

The method of the invention is further illustrated by the images shown in FIGS. 1 to 11.

$T_2$-weighted spin-echo (TR/TE 2800/180 msec) images of the cat brain were acquired following a unilateral MCA occlusion of one hour duration and subsequent reperfusion of the occluded artery.

At 108, 160 and 320 minutes following arterial reopening 0.5 mmol/kg Dy DTPA-BMA was injected intravenously over 90 seconds between phase encoding-step steps 32 and 60 of 128 phase encoding image acquisitions.

Figure 4:
Figure 7:
Figure 2:
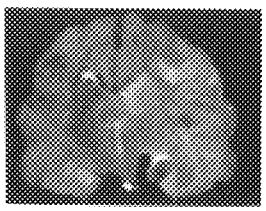
Figure 5:
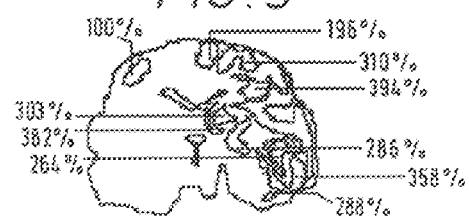
Figure 8:
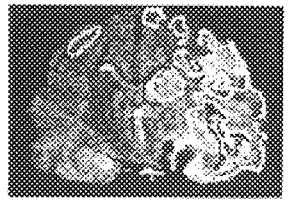
Figure 3:
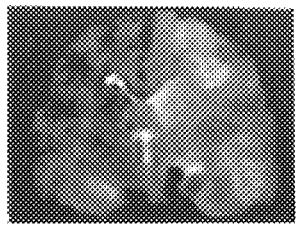
Figure 6:
Figure 9:
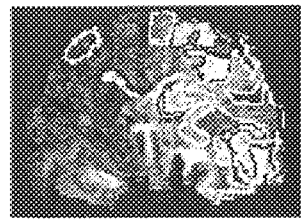

A section of the unaffected brain hemisphere was selected as a signal intensity reference (100%) and for each temporal image of the selected slice contours showing the degree of the hyperintensity of the affected hemisphere were plotted. The images at 108, 160 and 320 minutes post-occlusion are shown in FIGS. 1, 2 and 3. The corresponding contour maps of hyperintensity, i.e. blood perfusion deficit, are shown in FIGS. 4, 5 and 6 and, superimposed on the MR images, in FIGS. 7, 8 and 9.

Figure 10:
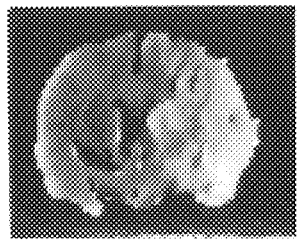
FIGS. 10–11 show, respectively, TTC-stained histopathologic cat brain sections and superimposed staining contours obtained in Study 2.
Figure 11:
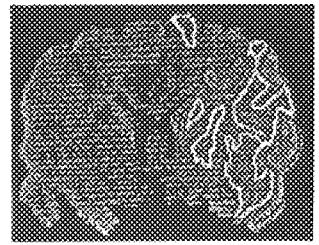

The accuracy of this technique in identifying the location, extent and severity of ischaemic damage is demonstrated by the corresponding TTC-stained histopathologic sections shown in FIG. 10 and, with superimposed staining contours, in FIG. 11.

These images illustrate a failed reperfusion which led ultimately to severe and extensive brain damage, which was corroborated by the histopathologic results.

Study 3

The method of the invention is further illustrated by the images shown in FIGS. 12 to 18.

Echo planar (EP) images (65 msec acquisition time) of the cat brain were recorded before, during and after a unilateral MCA occlusion, in each case with intravenous bolus injection of 0.25 mmol/kg DyDTPA-BMA between the first and second of sixteen sequential EP images.

Figure 12:
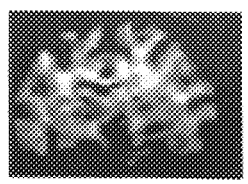
FIGS. 12–14 show echo planar images of a cat brain obtained before, during and after unilateral MCA occlusion and subsequent reperfusion (see Study 3).
Figure 14:
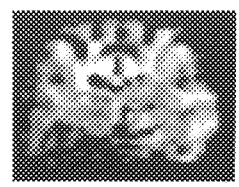
Figure 13:
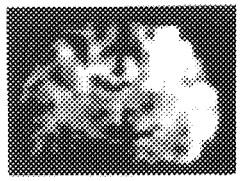
Figure 15:
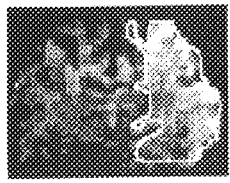
FIGS. 15–16 show, respectively, the 20% or greater hypersensitivity area and a contour map of hypersensitivity obtained during the cat brain occlusion of Study 3.
Figure 16A:
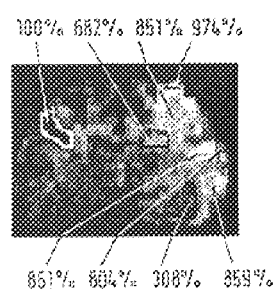
Figure 16B:
Figure 17:
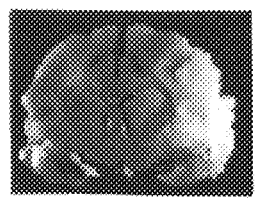
FIGS. 17–18 show TTC-stained histopathologic cat brain section obtained in Study 3.
Figure 18:
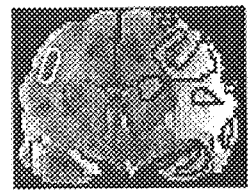

A region of the unaffected brain hemisphere was selected as a signal intensity reference (100%) and for each temporal image of the selected slice the extent and the severity of perfusion deficit was plotted. The images before occlusion, during occlusion and after successful reperfusion are shown in FIGS. 12, 13 and 14. The area showing 20% or greater hyperintensity, indicative of the extent of the perfusion deficit, is shown in FIG. 15 and a contour map of hyperintensity illustrating the areas of severe deficit is shown in FIG. 16, in each case for the image acquired during occlusion as the pre- and post-occlusion images did not show hyperintense regions. Once again the area and severity of blood flow reduction during occlusion thus identified closely correlates with the corresponding TTC-stained histopathologic sections as shown in FIGS. 17 and 18.

Study 4

The method of the invention is further illustrated by the images shown in FIGS. 19 to 22.

Figure 19A:
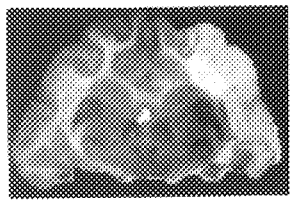
FIGS. 19–22 show brain images and intensity contour map of a 99Tc-HMPAO autoradiograph (FIG. 19), TTC-staining of a histopathologic section (FIG. 20), a $T_2$-weighted MR image without contrast agent (FIG. 21), and a $T_2$-weighted MR image with DyDTPA/BMA contrast agent (FIG. 22), as described in Study 4.
Figure 19B:
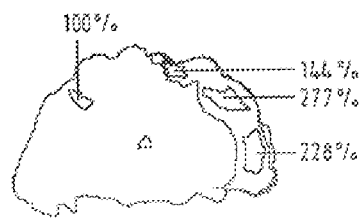
Figure 19C:
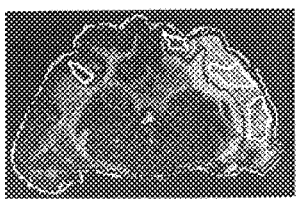
Figure 20A:
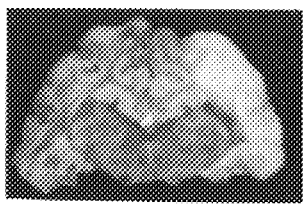
Figure 20B:
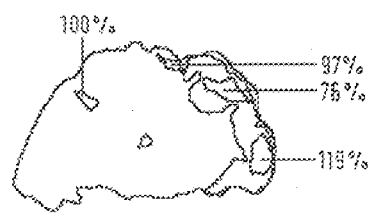
Figure 20C:
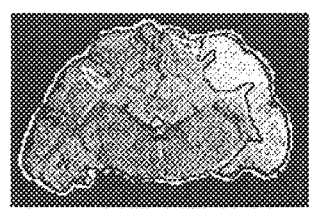
Figure 21A:
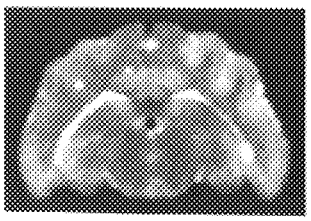
Figure 21B:
Figure 21C:
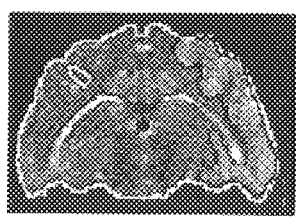
Figure 22A:
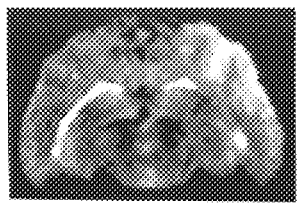
Figure 22B:
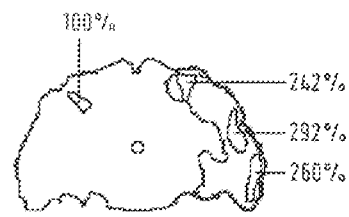
Figure 22C:
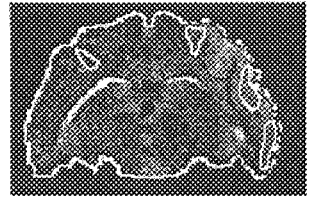

The information on extent and severity of perfusion deficit available using the method of the invention was compared with that available using conventional techniques of autoradiography (using 99Tc-HMPAO) and TTC histopathology. FIGS. 19a, b and c, 20a, b and c, 21a, b and c and 22a, b and c show respectively a 99Tc-HMPAO autoradiograph, TTC-staining of a histopathologic section, a $T_2$-weighted MR image (without contrast agent) and a $T_2$-weighted MR image following iv administration of 0.25 mmol/kg DyDTPA/BMA. The (a) images are the images as recorded, the (b) images show contour maps of regions of modified intensity (the selected reference (100%) regions are also shown) and the (c) images superimpose the raw images (a) and the contour maps (b). The correlation between the information from the autoradiograph (FIG. 19), which is currently accepted as being particularly accurate and sensitive to cerebral blood volume determination and from the images obtained according to the invention (FIG. 22) is particularly good.

Study 5

Figure 23A:
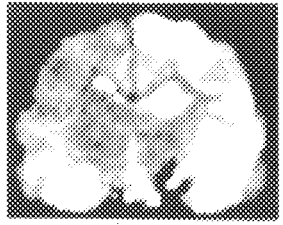
FIGS. 23–24 show $T_2$-weighted spin-echo images of a cat brain (FIGS. 23A and 24A), hyperintensity contour maps derived therefrom (FIGS. 23B and 24B), and superimposed versions (FIGS. 23C and 24C), acquired at 128 and 280 minutes following unilateral MCA occlusion (see Study 5).
Figure 23B:
Figure 23C:
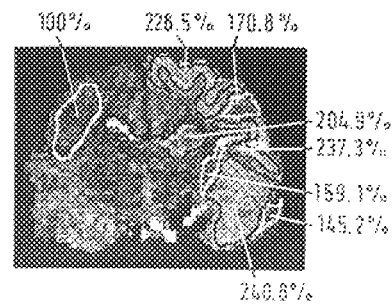
Figure 24A:
Figure 24B:
Figure 24C:
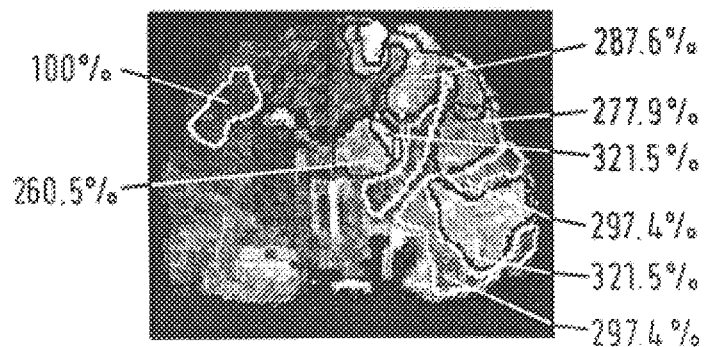

The method of the invention is further illustrated by the images shown in FIGS. 23 and 24.

$T_2$-weighted spin-echo (TR/TE 2800/180 msec) images of the cat brain were recorded during unilateral MCA occlusion, more particularly at 128 minutes and 280 minutes after arterial occlusion occurred. 0.25 mmol/kg DyDTPA/BMA was injected intravenously over 45 seconds between phase encoding steps 32 and 60 of the 128 phase encoding-step acquisitions. FIGS. 23a, b and c and 24a, b and c show the recorded images at 128 and 280 minutes (the (a) images), the contour maps of hypertensity (the (b) images showing the reference areas (100%) of the unaffected hemisphere) and the superpositions of the MR images and the contour maps (the (c) images). At 128 minutes seven different regions of perfusion deficiency were identified. This heterogenicity of the perfusion deficiency is to be expected early in the course of a cerebral ischaemia. At 280 minutes the increased levels of hyperintensity confirm worsening perfusion deficit in most brain regions but the heterogeneity of the hyperintensity suggests that some brain areas may still retain some blood flow.

We claim:

1. A method of monitoring surgically induced blood perfusion variations, said method comprising administering a contrast enhancing amount of an intravascular paramagnetic metal containing magnetic susceptibility magnetic resonance imaging contrast agent into the systemic vasculature of a human or animal body which is undergoing or has undergone surgery, subjecting said body to a magnetic resonance imaging procedure capable of generating from magnetic resonance signals from said body a series of temporally spaced images of at least a part of said body into which said agent passes, and detecting temporal variations in said signals or images whereby to identify regions of surgically induced variations in blood perfusion.

2. A method according to claim 1 wherein said contrast agent comprises a physiologically tolerable complex of a paramagnetic lanthanide ion or a physiologically tolerable salt of such a chelate.

3. A method according to claim 2 wherein said contrast agent is a chelate complex of a metal ion selected from the paramagnetic ions of Yb, Tm, Dy, Ho, Er and Gd, or a physiologically tolerable salt thereof.

4. A method according to claim 3 wherein said contrast agent is a chelate complex of Dy(III) or a physiologically tolerable salt thereof.

5. A method according to claim 1 wherein said contrast agent comprises a physiologically tolerable non-ionic paramagnetic lanthanide chelate complex.

6. A method according to claim 2 wherein said chelate complex is a complex of a linear, branched or macrocyclic chelant selected from polyaminopolycarboxylic acid chelants and from chelants wherein one or more carboxylic acid groupings are replaced with an amide, ester or hydroxamate grouping.

7. A method according to claim 6 wherein said chelate complex is a complex of a chelant selected from the group consisting of DTPA, DTPA-BMA, DOTA, DO3A, DPTA-BMO and HP-DO3A.

8. A method according to claim 2 wherein said chelate complex is DyDTPA-BMA.

9. A method according to claim 1 wherein said contrast agent is administered at a dosage of 0.02 to 3 mmol/kg bodyweight.

10. A method according to claim 1 wherein said contrast agent is administered at a dosage of 0.08 to 0.5 mmol/kg bodyweight.

11. A method according to claim 1 wherein said magnetic resonance imaging procedure is a fast imaging procedure.

12. A method according to claim 11 wherein said fast imaging procedure is one having an image acquisition time of less than 5 seconds.

13. A method according to claim 11 wherein said fast imaging procedure is one having an image acquisition time of less than 0.5 seconds.

14. A method according to claim 1 wherein said magnetic resonance imaging procedure is an echo planar imaging procedure.

15. A method according to claim 1 comprising generating temporally spaced $T_2^*$ or $T_2$-weighted images.

16. A method according to claim 15 wherein said magnetic resonance imaging procedure is a spin-echo or gradient echo procedure.

17. A method according to claim 15 comprising generating and comparing $T_1$-weighted images or signals transformable thereto and $T_2^*$ or $T_2$-weighted images or signals transformable thereto whereby to identify body regions in which blood perfusion occurs.

18. A method according to claim 1 being a method of detecting body regions of blood flow deficit.

19. A method according to claim 18 being a method of detecting ischemic regions.

20. A method according to claim 1 wherein said contrast agent comprises a physiologically tolerable complex of a paramagnetic transition metal ion or a physiologically tolerable salt of such a chelate.

21. A method according to claim 1 wherein said contrast agent is administered as a contrast medium composition comprising DyDTPA-BMA and CaNaDTPA-BMA in a molar ratio of about 20:1.

* * * * *